(12) United States Patent
Lee

(10) Patent No.: US 11,529,296 B2
(45) Date of Patent: *Dec. 20, 2022

(54) WATER-RELEASING STICK-TYPE COSMETIC

(71) Applicant: SUNJIN BEAUTY SCIENCE CO., LTD., Ansan-si (KR)

(72) Inventor: Sung Ho Lee, Ansan-si (KR)

(73) Assignee: Sunjin Beauty Science Co., Ltd., Ansan-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/969,631

(22) PCT Filed: Jun. 14, 2018

(86) PCT No.: PCT/KR2018/006697
§ 371 (c)(1),
(2) Date: Aug. 13, 2020

(87) PCT Pub. No.: WO2019/182198
PCT Pub. Date: Sep. 26, 2019

(65) Prior Publication Data
US 2020/0405597 A1 Dec. 31, 2020

(30) Foreign Application Priority Data

Mar. 19, 2018 (KR) .................. 10-2018-0031386
May 18, 2018 (KR) .................. 10-2018-0057024

(51) Int. Cl.
| | | |
|---|---|---|
| *A61K 8/25* | (2006.01) | |
| *A61K 8/02* | (2006.01) | |
| *A61K 8/06* | (2006.01) | |
| *A61K 8/92* | (2006.01) | |
| *A61Q 1/06* | (2006.01) | |
| *A61Q 1/04* | (2006.01) | |
| *A61Q 17/04* | (2006.01) | |

(52) U.S. Cl.
CPC ............. *A61K 8/25* (2013.01); *A61K 8/0229* (2013.01); *A61K 8/06* (2013.01); *A61K 8/92* (2013.01); *A61Q 1/04* (2013.01); *A61Q 1/06* (2013.01); *A61Q 17/04* (2013.01); *A61K 2800/56* (2013.01); *A61K 2800/651* (2013.01)

(58) Field of Classification Search
None
See application file for complete search history.

(56) References Cited

U.S. PATENT DOCUMENTS

| | | | | |
|---|---|---|---|---|
| 4,446,051 | A * | 5/1984 | Berthod ................... | A61K 8/19 516/23 |
| 2014/0080924 | A1* | 3/2014 | Rigg ..................... | A61K 8/345 514/788 |
| 2015/0174043 | A1* | 6/2015 | Chiou .................... | A61K 8/891 424/78.03 |
| 2017/0135912 | A1* | 5/2017 | Perrin .................. | A61K 8/8117 |

FOREIGN PATENT DOCUMENTS

| | | |
|---|---|---|
| KR | 10-2003-0030429 | 4/2003 |
| KR | 10-2005-0053922 | 6/2005 |
| KR | 10-2013-0049053 | 5/2013 |
| KR | 20170126259 * | 5/2016 |
| KR | 10-2016-0065658 A | 6/2016 |

OTHER PUBLICATIONS

Voorn et al. "Polymer-clay nanocomposite latex particles by inverse Pickering emulsion polymerization stabilized with hydrophobic montmorillonite platelets" Macromolecules, vol. 39, No. 6, p. 2137-2143 2006.*
Le Reverend et al. "Design and application of water-in-oil-emulsions for use in lipstick formulations" International Journal of Cosmetic Science, 2011, 1-8.*

* cited by examiner

*Primary Examiner* — Danah Al-Awadi
(74) *Attorney, Agent, or Firm* — Lex IP Meister, PLLC

(57) ABSTRACT

The present invention relates to a water-releasing stick-type cosmetic and, specifically, to a water-releasing stick-type cosmetic containing: an oily portion; and a water-releasing ingredient that is spread out in the oily portion, wherein the water-releasing ingredient has water particles encompassed by a plurality of plate-shaped materials to which emulsifiers are bound. According to the present invention, provided is a water-releasing stick-type cosmetic, which can provide a moist and cool feeling by directly supplying a large quantity of water, has excellent dosage form stability by having a hardness suitable for stick cosmetics, and simultaneously has excellent application texture, excellent storage stability and excellent color tone.

3 Claims, 2 Drawing Sheets

[FIG. 1]
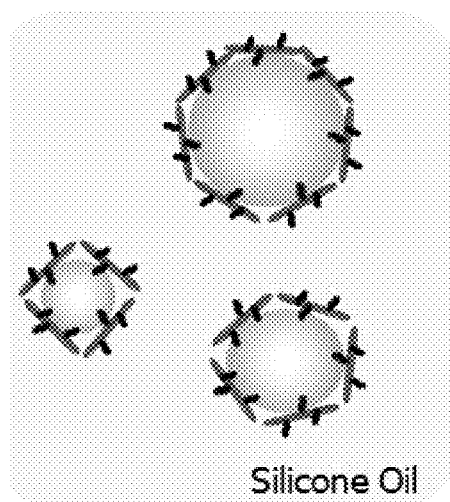
Silicone Oil
[FIG. 2]
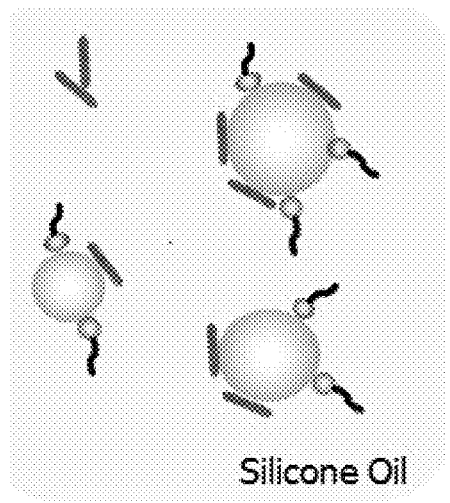
Silicone Oil

[FIG. 3]
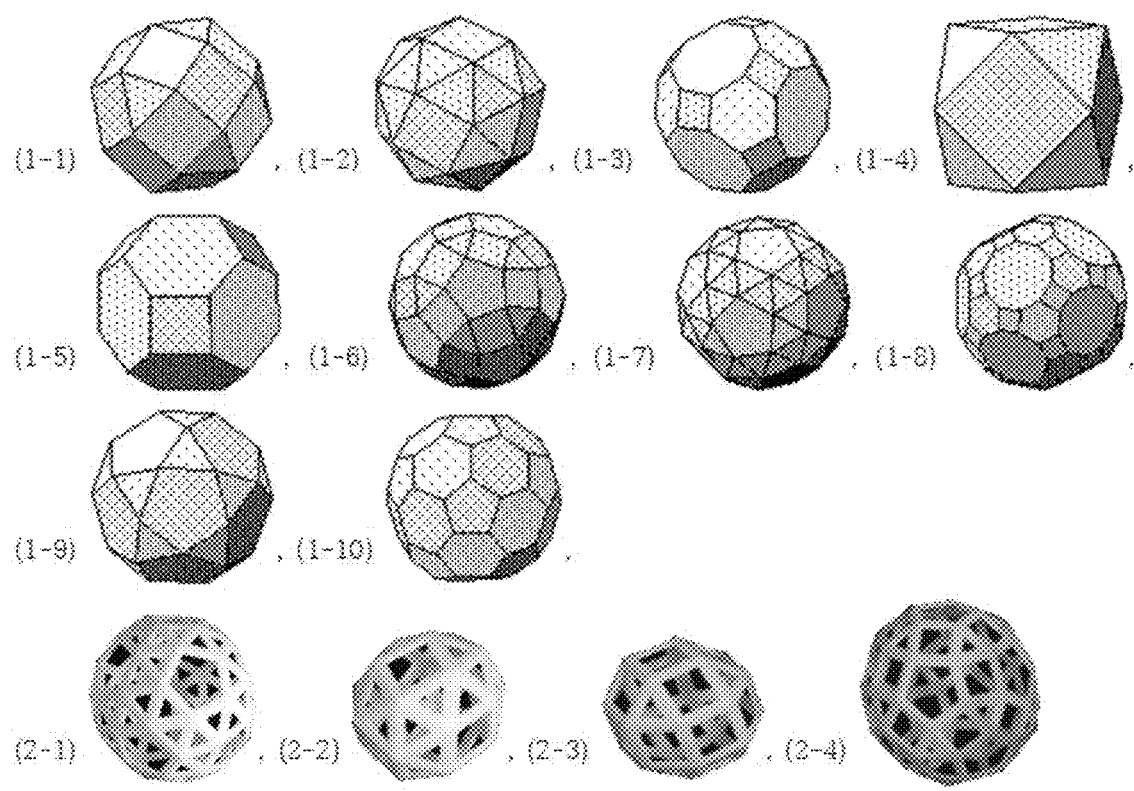

WATER-RELEASING STICK-TYPE COSMETIC

TECHNICAL FIELD

The present invention relates to a water-releasing stick-type cosmetic, and more particularly, to a water-releasing stick-type cosmetic which is capable of directly supplying a large amount of moisture to provide moisturization and coolness, has hardness suitable for stick cosmetics to have excellent formulation stability, has excellent spreadability, has excellent storage stability, and concurrently has excellent color tone, and a method of manufacturing the same.

BACKGROUND ART

The following description merely provides background information related to the present invention and may not constitute the related art.

Stick-type cosmetics are advantageous for use and storage because a formulation thereof is in a solid phase as compared with general cosmetics. Due to the advantage of such a stick-type cosmetic, an attempt has been made to manufacture cosmetics for many applications in the form of a stick.

Since the stick-type cosmetic is applied directly to a skin without using a hand, the stick-type cosmetic is required to have appropriate hardness in order to maintain spreadability and a stick-like shape when the stick-type cosmetic is applied.

In addition, when a stick-type cosmetic includes moisture and the moisture is supplied directly to a skin, there are advantages in that sufficient moisture may be easy to supply and a cool feeling may be provided during makeup. Thus, an attempt has constantly been made to add moisture to a stick-type cosmetic. However, when moisture is included in the stick-type cosmetic, there is a problem in that formulation stability of a stick-type is significantly reduced.

In order to solve the problem, in Korean Patent Publication No. 1999-0069366, 5.0 wt % to 20.0 wt % of polar ester, which is selected from the group consisting of diglyceryl isostearate, diglyceryl diisostearate, and diglyceryl triisostearate, forms a gel network together with a hydrophilic moisturizer, thereby providing a lipstick composition having hardness suitable for a lipstick. However, there is a limitation in that moisture cannot be directly supplied.

In addition, in Korean Patent Publication No. 10-2016-0139042, volatile fluid oil, wax capable of pectizing an oil component, a silicone elastomer, and a silicon-based surfactant are mixed to form a water-in-oil type emulsion including a large amount of water, thereby providing a stick-shaped cosmetic capable of being applied on a skin to supply moisture to the skin. However, there is a problem in that the stick-shaped cosmetic has a limitation in storage stability.

In particular, in the case of lip cosmetics, a water-dispersion type lip cosmetic composition including sodium polyacrylate starch, which may be applied on the existing lipstick after the existing lipstick is applied in order to supply moisture, has been introduced. However, since the existing lipstick and the separate water-dispersion type lip cosmetic composition are used, significant inconvenience in use is caused. Therefore, there is an urgent need for a stick-type cosmetic in which moisture is released from one lipstick.

DISCLOSURE

Technical Problem

The present invention is directed to providing a water-releasing stick-type cosmetic which is capable of directly supplying a large amount of moisture to provide moisturization and coolness, has hardness suitable for stick cosmetics to have excellent formulation stability, has excellent spreadability, has excellent storage stability, and concurrently has excellent color tone, and a method of manufacturing the same.

Technical Solution

The present invention is directed to solving above problems.

The present invention provides a water-releasing stick-type cosmetic.

The water-releasing stick-type cosmetic includes an oil phase portion, and a moisture-releasing component.

The moisture-releasing component is spread in the oil phase portion.

The moisture-releasing component is characterized in that particles of moisture are surrounded by a plurality of plate-like materials.

An emulsifier is combined to the plurality of plate-like materials.

A content of the moisture may be in a range of 20 wt % to 60%.

The water-releasing stick-type cosmetic may have a hardness of 10 Newtons to 250 Newtons.

The plurality of plate-like materials, to which the emulsifier is combined, may form a thixotropic polyhedron.

A polyhedral composite may have a shape of 5-hedron to 500-hedron.

The plate-like material may be disteardimonium hectorite.

The plate-like material may have a height of 0.0005 μm to 0.005 μm.

The emulsifier may include a $C_9$ to $C_{22}$ alkyl residue.

The particles of the moisture may have a diameter of 1 μm to 100 μm.

The particles of the moisture and the plurality of plate-like materials to which the emulsifier is combined may be included in a ratio of 80 to 99 parts by weight to 1 to 20 parts by weight.

The water-releasing stick-type cosmetic may be used in a lipstick, a lip gloss, a lip balm, a lip tint, a vivistick, or a sun stick.

The present invention provides a method of manufacturing a water-releasing stick-type cosmetic.

The method includes operations S1) to S4).

Operation S1) is an operation of spraying a plurality of plate-like materials at a pressure of 100 bar to 600 bar using a nozzle to mix the plurality of plate-like materials with an emulsifier.

The nozzle has a size of 1 μm to 50 μm.

Operation S2) is an operation of mixing an oil phase component into the resultant mixture of operation S1).

Operation S3) is an operation of mixing an aqueous phase component into the resultant mixture of operation S2).

Operation S4) is an operation of filling the resultant mixture of operation S3) in a stick molding container and then cooling the mixture.

In operation S1), oil may be further mixed.

The mixing of operation S3) may be performed at a stirring speed of 1,800 rpm to 2,500 rpm using a homogenizer.

Advantageous Effects

A water-releasing stick-type cosmetic according to the present invention may directly supply a large amount of moisture, have hardness suitable for stick cosmetics to have excellent formulation stability, have excellent spreadability, have excellent storage stability, and concurrently have excellent color tone.

DESCRIPTION OF DRAWINGS

FIG. 1 is a schematic diagram view two-dimensionally illustrating a moisture-releasing component of a water-releasing stick-type cosmetic according to one embodiment of the present invention.

FIG. 2 is a schematic diagram two-dimensionally illustrating an aqueous phase component of a stick-type cosmetic when a plate-like material and an emulsifier are simply mixed.

FIG. 3 illustrates examples of a three-dimensional schematic diagram of a polyhedral composite of the moisture-releasing cosmetic according to one embodiment of the present invention.

MODES OF THE INVENTION

Hereinafter, embodiments of the present invention will be described in detail with reference to the accompanying drawings so that those skilled in the art to which the present invention pertains can realize the present invention. The present invention may, however, be embodied in different forms and should not be construed as being limited to the embodiments set forth herein. In the drawings, certain parts not directly relevant to the description are omitted to enhance the clarity of the present invention, and like reference numerals denote like parts throughout the whole document.

It will be further understood that the terms "comprises", "comprising", "includes," and/or "including", when used herein, specify the presence of stated elements, but do not preclude the presence or addition of one or more other elements, unless the context clearly indicates otherwise.

FIG. 1 is a schematic diagram view two-dimensionally illustrating a moisture-releasing component of a water-releasing stick-type cosmetic according to one embodiment of the present invention. FIG. 2 is a schematic diagram two-dimensionally illustrating an aqueous phase component of a stick-type cosmetic when a plate-like material and an emulsifier are simply mixed. FIG. 3 illustrates examples of a three-dimensional schematic diagram of a polyhedral composite of the moisture-releasing cosmetic according to one embodiment of the present invention.

The water-releasing stick-type cosmetic of the present invention includes an oil phase portion and the moisture-releasing component spreading in the oil phase portion. The moisture-releasing component is characterized in that moisture particles are surrounded by a plurality of plate-like materials to which an emulsifier is combined.

In the water-releasing stick-type cosmetic according to the present invention, as shown in FIG. 1, the moisture-releasing component has a shape in which the plurality of plate-like materials, to which the emulsifier is combined, surround moisture particles in the form of a polyhedral composite in the stick-type cosmetic and the polyhedral composite is transformed by an application during use of the water-releasing stick-type cosmetic to release moisture. The polyhedral composite may be formed through a bond have thixotropic properties between adjacent plate-like materials surrounding moisture particles in the cosmetic.

In the present invention, the plate-like material may have a surface that has a lipophilic property and may have a corner that includes a hydroxy group. Specifically, a material, which is obtained by swelling and separating a smectite clay mineral into individual plate-like materials, and then, substituting surfaces of the plate-like materials with a lipophilic material, may be used as the plate-like material. A commercially available product may be purchased and used as the individually separated plate-like material, and as an example, a product manufactured by Elementis Co. Ltd may be used.

The smectite clay mineral is not particularly limited. Specifically, the smectite clay mineral may be hectorite or bentonite and preferably may be hectorite. In this case, it is possible to manufacture a water-releasing stick-type cosmetic having more excellent formulation stability.

The lipophilic material is not particularly limited as long as the lipophilic material may impart lipophilicity to a surface of the plate-like material. Specifically, the lipophilic material may be a material including a $C_5$ to $C_{22}$ aliphatic alkyl residue. More specifically, the material including the $C_5$ to $C_{22}$ aliphatic alkyl residue may be a quaternary ammonium salt.

Preferably, the plate-like material may be disteardimonium hectorite.

A shape of a surface of the plate-like material is not particularly limited, and the plate-like material may be circular, triangular, or amorphous material and may be a mixture of two or more materials.

In addition, the plate-like material may be selected by arbitrarily adjusting a thickness and lengths of a major axis and a minor axis thereof. Specifically, the thickness may be in a range of 0.0005 μm to 0.005 μm, and the long axis may be in a range of 0.5 μm to 1.5 μm. When the thickness and the long axis are within the ranges, it is possible to provide a cosmetic that includes a large amount of moisture and also has excellent formulation stability.

The plate-like material may be a mixture of two or more different materials. For example, a material having a long axis of 0.8 μm and a material having a long axis of 1.2 μm may be mixed and used as the plate-like material.

In the present invention, the emulsifier is not particularly limited as long as the emulsifier is an emulsifier that is usable in cosmetics. An emulsifier is not limited as long as the emulsifier is compatible with an oil phase component according to the use of the oil phase component according to the use of the water-releasing stick-type cosmetic according to the present invention. Preferably, the emulsifier may be an emulsifier including a $C_9$ to $C_{22}$ alkyl residue. In this case, it is possible to provide a cosmetic including a large amount of moisture and also having excellent formulation stability. As specific examples of the emulsifier, polyglyceryl-4 isostearate, polyglyceryl-3 polyricinoleate, polyglyceryl-3 diisostearate, polyglyceryl-4 oleate, polyglyceryl-4 diisostearate/polyhydroxystearate/sebacate, diisostearoyl polyglyceryl-3 dimer dilinoleate, polyglyceryl-3 polyricinoleate, sorbitan isostearate, glyceryl laurate, sorbitan oleate, sorbitan sesquioleate, lauryl PEG-9 polydimethylsiloxyethyl dimethicone, PEG-9 Polydimethylsiloxyethyl dimethicone, and PEG-10 dimethicone may be used alone or in combination of two or more thereof.

In the present invention, a content of the plate-like material and a content of the emulsifier may be in a ratio of 0.9 to 10 parts by weight to 0.1 to 10 parts by weight. When the contents of the plate-like material and the emulsifier are within the ranges, it is possible to provide a cosmetic that includes a large amount of moisture and has excellent formulation stability.

In addition, in the stick-type cosmetic of the present invention, a moisture component may be in an aqueous phase (water) as a specific example. If necessary, the moisture component may be moisture in which known components useable in a cosmetic is dissolved. As specific examples of the known components, ions, fragrances, extracts, nutrients, moisturizers, or other functional components used in cosmetics may be included in a use amount of typical additives (range of 0.001 wt % to 10 wt %). Two or more known components may be mixed and used.

In the present invention, a content of the plurality of plate-like materials to which the emulsifier is combined, and a content of the moisture component may be arbitrarily adjusted and may be in a ratio of 1 to 20 parts by weight to 80 to 99 parts by weight. In this case, it is possible to provide a cosmetic including a large amount of moisture and also having excellent formulation stability.

In the present invention, the polyhedral composite may have a shape of 5-hedron to 500-hedron, have a two-dimensional shape of a polyhedron as shown in FIG. 1, and have a three-dimensional shape of one of polyhedrons as shown in FIG. 3. In addition, the polyhedral composite may have a structure in which pores are blocked as shown in 1-1 to 1-10 of FIG. 3 or have a structure having pores as shown in 2-1 to 2-4 of FIG. 3. The polyhedral composite may have a structure of which corners are smooth and also have a structure in which some of the plate-like materials protrude. When there are pores, a cross-sectional size of the maximum pore may be within 50% of a maximum cross-sectional size of the moisture particles, and preferably, may be within 10% of the maximum cross-sectional size of the moisture particles. In this case, when the cross-sectional size of the maximum pore is within the range, it is possible to provide a cosmetic that includes a large amount of moisture and also has excellent formulation stability.

In the water-releasing stick-type cosmetic of the present invention, the moisture-releasing component may have a diameter of 1 μm to 100 μm, and preferably, 10 μm to 60 μm. In this case, when a cosmetic is used, it is easy to release moisture by an application of the cosmetic, and a formulation stability of the cosmetic is more excellent. When a size of the moisture-releasing component is too small, it is difficult to add a large amount of moisture, and when a cosmetic is used, it is not easy to release moisture. When the size of the moisture-releasing component is too large, stability of the moisture-releasing component may be lowered in the cosmetic.

Use of the water-releasing stick-type cosmetic of the present invention is not particularly limited. As a specific example, the water-releasing stick-type cosmetic may be used in a lipstick, a lip gloss, a lip balm, a lip tint, a vivistick, or a sun stick.

The water-releasing stick-type cosmetic of the present invention may include a known oil phase component suitable for use. Specific examples of the oil phase component may include oil applicable to stick-type cosmetics, wax applicable to stick-type cosmetics, a polymer resin applicable to stick-type cosmetics, and vegetable oil applicable to stick-type cosmetics. The oil, wax, polymer resin, or vegetable oil may be used alone or in combination of two or more thereof.

In addition, the water-releasing stick-type cosmetic of the present invention may optionally include known additional components used in stick-type cosmetics. As specific examples of the additional components, powders, thickeners, fungicides, preservatives, vitamins, and functional medicines may each independently be included.

Of course, in the water-releasing stick-type cosmetic of the present invention, the oil phase component and the additional components may be arbitrarily adjusted according to use. As a specific example, the oil phase component and the additional components may each independently be arbitrarily adjusted within a range of 0.001 wt % to 50 wt % in the stick-type cosmetic.

The water-releasing stick-type cosmetic of the present invention may include a large amount of moisture through the moisture-releasing component peculiar to the present invention, and a content of the moisture may be preferably in a range of 20 wt % to 60 wt %. More preferably, a content of the moisture may be preferably in a range of 30 wt % to 57 wt %. In this case, formulation stability, storage stability, and spreadability may be concurrently satisfied.

In addition, the water-releasing stick-type cosmetic of the present invention has hardness suitable for stick-type cosmetics. Specifically, the hardness may be in a range of 10 Newtons to 250 Newtons (measured using SUN RHEO METER manufactured by Sun Scientific Company (Japan)). In this case, formulation stability and spreadability may be concurrently satisfied.

The water-releasing stick-type cosmetic according to the present invention may be manufactured through a method of manufacturing a water-releasing stick-type cosmetic, the method including S1) spraying a plurality of plate-like materials at a pressure of 100 bar to 600 bar using a nozzle having a size of 1 μm to 50 μm to mix the plurality of plate-like materials with an emulsifier, S2) mixing an oil phase component into the resultant mixture of operation S1), S3) mixing an aqueous phase component into the resultant mixture of operation S2), and S4) filling the resultant mixture of operation S3) in a stick molding container and then cooling the mixture. A content ratio of the water-releasing stick-type cosmetic may be applied to a content ratio of the components used in the method of manufacturing a water-releasing stick-type cosmetic of the present invention.

Since the method of manufacturing a water-releasing stick-type cosmetic of the present invention includes S1) spraying the plurality of plate-like materials at a pressure of 100 bar to 600 bar using the nozzle having a size of 1 μm to 50 μm to mix the plurality of plate-like materials with the emulsifier, it is possible to allow a moisture-releasing component peculiar to the present invention to be included in the cosmetic. In a conventional general mixer, as shown in FIG. 2, the polyhedral composite of the present invention is not formed, but when the plurality of plate-like materials are mixed with the emulsifier through operation S1) and then operations S2) to S4) are performed, a bond having thixotropic properties may occur, and thus, the polyhedral composite may be formed as shown in FIG. 1.

In operation S1) of the present invention, vegetable oil may be further mixed. A content of the vegetable oil may be arbitrarily adjusted, but the vegetable oil may be mixed in an amount of 10 to 100 parts by weight with respect to 100 parts by weight of the total of the plate-like material and the emulsifier. In this case, formulation stability of the water-release stick-type cosmetic may be further improved.

In the present invention, a process of mixing an oil phase component used in a mixing process of a known stick-type cosmetic may be applied to operation S200 of mixing the oil phase component into the mixture of operation S1), except that the mixture of operation S1) is used. For example, the mixing may use a homogenizer or a 3-roll mill. When a powder component is included in the present invention, the powder component may be further mixed when the oil phase component of operation S2) is mixed.

In the present invention, the mixing of operation S3) may be performed using a known mixer that mixes an oil phase component and an aqueous phase component, and for example, the mixing may be performed by performing stirring using a homogenizer or a stirrer. Preferably, the mixing may be performed at a stirring speed of 1,800 rpm to 2,500 rpm. In this case, a size of moisture particles is suitable for the water-releasing stick-type cosmetic of the present invention so that it is possible to manufacture a water-releasing stick-type cosmetic including a large amount of moisture and also having excellent formulation stability. In addition, if necessary, after the mixing of operation S3), a fragrance component may be further mixed to provide fragrance to a cosmetic.

In the present invention, of course, a method applies to a known stick cosmetic may be applied to operation S4) of filling the mixture of operation S3) in the stick molding container.

A water-releasing stick-type cosmetic manufactured through of the method of manufacturing a water-releasing stick-type cosmetic of the present invention may include an oil phase portion and a moisture-releasing component spreading in the oil phase portion. The moisture-releasing component may have a shape in which moisture particles are surrounded by a plurality of plate-like materials to which an emulsifier is combined, and thus, the water-releasing stick-type cosmetic may include a large amount of moisture and also have excellent formulation stability and storage stability.

Hereinafter, Examples of the present invention will be described in detail for better understanding. However, Examples of the present invention may be modified in various ways, and the scope of the present invention should not be interpreted as being limited to Examples described below. Examples of the present invention are just for better understanding of the present invention to persons having ordinary skill in the art.

Example 1 (Lipstick)

1.5 parts by weight of polyglyceryl-4 isostearate, 1.5 parts by weight of polyglycerol-3 polyricinoleate, 1.6 parts by weight of sorbitan isostearate, and 3.0 parts by weight of disteardimonium hectorite were sprayed at a pressure of 100 bar to 600 bar using a nozzle having a size of 1 μm to 50 μm to be mixed into each other. As oil phase components, 8 parts by weight of hydrogenated polydecene, 5 parts by weight of squalane, 4 parts by weight of caprylic/capric triglyceride, 3 parts by weight of diisostearyl malate, 4 parts by weight of dipentaerythrityl hexahydroxystearate/hexastearate/hexarosinate (trade name Cosmol 168AR), 3 parts by weight of microcrystalline wax, 7 parts by weight of ozokerite, 6.5 parts by weight of ceresin, 2 parts by weight of titanium dioxide & triethoxy caprylylsilane (trade name: SUNTI-TAN-AS), 1.5 parts by weight of red iron oxide & triethoxy caprylylsilane (trade name SUNIOR-AS), and 2 parts by weight of mica & polymethyl methacrylate & titanium dioxide (trade name JH-RED) were mixed into the resultant mixture at a temperature of 70° C. to 75° C. using a 3-roll mill to prepare an oil phase mixture. 34.6 parts by weight of water, 6 parts by weight of butylene glycol, 2.0 parts by weight of 1,2-hexanediol, and 0.4 parts by weight of fragrance were mixed at a temperature of 40° C. to prepare an aqueous phase component. The prepared oil phase mixture and aqueous phase component were stirred at a stirring speed of 1,800 rpm to 2,500 rpm using a stirrer and mixed to manufacture a lipstick cosmetic. The lipstick cosmetic was introduced into a mold and cooled to manufacture a final lipstick. Hardness was measured using SUN RHEO METER (manufactured by Sun Scientific Company (Japan)) and was in a range of 10 Newtons to 250 Newtons, which is suitable for a lipstick cosmetic.

Example 2 (Lipstick)

A lipstick was manufactured in the same manner as in Example 1, except that 1.5 parts by weight of polyglyceryl-4 isostearate, 1.5 parts by weight of polyglycerol-3 polyricinoleate, 1.6 parts by weight of sorbitan isostearate, 3.0 parts by weight of disteardimonium hectorite, and 3.4 parts by weight of coco-caprylate/caprate (trade name Cetiol C 5C) were sprayed at a pressure of 100 bar to 600 bar using a nozzle having a size of 1 μm to 50 μm to be mixed into each other. Hardness was measured using SUN RHEO METER (manufactured by Sun Scientific Company (Japan)) and was in a range of 10 Newtons to 250 Newtons, which is suitable for a lipstick cosmetic.

Comparative Example 1

A lipstick was manufactured in the same manner as in Example 1, excluding 3.0 parts by weight of disteardimonium hectorite, a spraying and mixing process performed at a pressure of 100 bar to 600 bar using a nozzle having a size of 1 μm to 50 μm, and a process of mixing components of an oil phase mixture at once using a 3-roll mil from Example 1.

Stability Comparison Experiment of Examples 1 and 2 and Comparative Example 1

After the lipsticks of Examples 1 and 2 and the lipstick of Comparative Example 1 were left at a temperature of 45° C. for 7 days, initial weights of the lipsticks were compared, and results thereof were shown in Table 1 below.

TABLE 1

| Classification | Initial weight(g) | Weight after 7 days (g) |
| --- | --- | --- |
| Example 1 | 3.49 | 3.43 |
| Example 2 | 3.50 | 3.46 |
| Comparative Example 1 | 3.48 | 2.31 |

As shown in Table 1, in the case of Examples according to the present invention, there was almost no change in weight, but in the case of Comparative Example 1, most moisture was evaporated. Thus, it may be confirmed that formulation stability of the lipstick of the present invention is considerably excellent.

Example 3 (Lip Tint)

1.5 parts by weight of polyglyceryl-4 isostearate, 1.5 parts by weight of polyglycerol-3 polyricinoleate, 1.6 parts by weight of sorbitan isostearate, and 3.0 parts by weight of disteardimonium hectorite were sprayed at a pressure of 100 bar to 600 bar using a nozzle having a size of 1 µm to 50 µm to be mixed into each other. As oil phase components, 12 parts by weight of coco-caprylate/caprate (trade name: Cetiol C 5C), 2 parts by weight of microcrystalline wax, 1 part by weight of stearyl heptanoate, 1 part by weight of shea butter, 13.5 parts by weight of ozokerite, 0.8 parts by weight of Fd&c Yellow No. 6 A1. (trade name: CI 15985), 0.8 parts by weight of Red No. 102 (trade name: CI 16255), and 6 parts by weight of D&C Red 28 A1. Lk (trade name: CI 45410) were mixed into the resultant mixture at a temperature of 70° C. to 75° C. using a 3-roll mill to prepare an oil phase mixture. 45.5 parts by weight of water, 6 parts by weight of butylene glycol, 2.0 parts by weight of 1,2-hexanediol, and 3 parts by weight of glycerin were mixed at a temperature of 40° C. to prepare an aqueous phase component. The prepared oil phase mixture and aqueous phase component were stirred at a stirring speed of 1,800 rpm to 2,500 rpm using a stirrer and mixed, and then, 0.3 parts by weight of a fragrance was mixed thereinto to manufacture a lip tint. The lip tint cosmetic was introduced into a mold and cooled to manufacture a final lip tint. Hardness was measured using SUN RHEO METER (manufactured by Sun Scientific Company (Japan)) and was in a range of 10 Newtons to 250 Newtons, which is suitable for a lip tint cosmetic.

Example 4 (Lip Tint)

A lip tint was manufactured in the same manner as in Example 3, except that 1.5 parts by weight of polyglyceryl-4 isostearate, 1.5 parts by weight of polyglycerol-3 polyricinoleate, 1.6 parts by weight of sorbitan isostearate, 3.0 parts by weight of disteardimonium hectorite, and 3.4 parts by weight of coco-caprylate/caprate (trade name Cetiol C 5C) were sprayed at a pressure of 100 bar to 600 bar using a nozzle having a size of 1 µm to 50 µm to be mixed into each other. Hardness was measured using SUN RHEO METER (manufactured by Sun Scientific Company (Japan)) and was in a range of 10 Newtons to 250 Newtons, which is suitable for stick cosmetics.

Comparative Example 2

A lipstick was manufactured in the same manner as in Example 3, excluding 3.0 parts by weight of disteardimonium hectorite, a spraying and mixing process performed at a pressure of 100 bar to 600 bar using a nozzle having a size of 1 µm to 50 µm, and a process of mixing components of an oil phase mixture at once using a 3-roll mil from Example 3.

Stability Comparison Experiment of Examples 3 and 4 and Comparative Example 2

After the lip tints of Examples 3 and 4 and the lip tint of Comparative Example 2 were left at a temperature of 50° C. for 7 days, initial weights of the lip tint were compared, and results thereof were shown in Table 2 below.

TABLE 2

| Classification | Initial weight(g) | Weight after 7 days (g) |
| --- | --- | --- |
| Example 3 | 15.07 | 14.63 |
| Example 4 | 14.89 | 14.57 |
| Comparative Example 2 | 14.92 | 8.36 |

[90] As shown in Table 2, in the case of Examples according to the present invention, there was almost no change in weight, but in the case of Comparative Example 2, most moisture was evaporated. Thus, it may be confirmed that formulation stability of the lip tint of the present invention is considerably excellent.

Example 5 (Sun Stick)

0.5 parts by weight of polyglyceryl-4 isostearate, 0.5 parts by weight of polyglycerol-3 polyricinoleate, 0.5 parts by weight of sorbitan isostearate, and 2.0 parts by weight of disteardimonium hectorite were sprayed at a pressure of 100 bar to 600 bar using a nozzle having a size of 1 µm to 50 µm to be mixed into each other. As oil phase components, 7.5 parts by weight of ethylhexyl methoxycinnamate, 5 parts by weight of ethylhexyl salicylate, 2.5 parts by weight of octocrylene, 8 parts by weight of C12 to C15 alkyl benzoate (trade name: Saboderm AB), 5 parts by weight of bis-ethylhexyloxyphenol methoxyphenyl triazine, 10 parts by weight of ozokerite, 5 parts by weight of microcrystalline wax, 6 parts by weight of zinc oxide & triethoxycaprylylsilane (trade name SUNZnO-NAS), and 3 parts by weight of titanium dioxide & alumina & triethoxycaprylylsilane (trade name TX-85) were mixed into the resultant mixture at a temperature of 70° C. to 75° C. using a 3-roll mill to prepare an oil phase mixture. 40.9 parts by weight of water, 1 part by weight of butylene glycol, 1 part by weight of glycerin, and 0.1 parts by weight of disodium EDTAT were mixed at a temperature of 40° C. to prepare an aqueous phase component. The prepared oil phase mixture and aqueous phase component were stirred at a stirring speed ranging from 1,800 rpm to 2,500 rpm using a stirrer and mixed to manufacture a sun stick. The sun stick cosmetic was introduced into a mold and cooled to manufacture a final sun stick. Hardness was measured using SUN RHEO METER (manufactured by Sun Scientific Company (Japan)) and was in a range of 10 Newtons to 250 Newtons, which is suitable for stick cosmetics.

Example 6 (Sun Stick)

A sun stick was manufactured in the same manner as in Example 5, except that 0.5 parts by weight of polyglyceryl-4 isostearate, 0.5 parts by weight of polyglycerol-3 polyricinoleate, 0.5 parts by weight of sorbitan isostearate, 2.0 parts by weight of disteardimonium hectorite, and 1.5 parts by weight of coco-caprylate/caprate (trade name Cetiol C 5C) were sprayed at a pressure of 100 bar to 600 bar using a nozzle having a size of 1 µm to 50 µm to be mixed into each other. Hardness was measured using SUN RHEO METER (manufactured by Sun Scientific Company (Japan)) and was in a range of 10 Newtons to 250 Newtons, which is suitable for stick cosmetics.

Comparative Example 3

A sun stick was manufactured in the same manner as in Example 5, excluding 2.0 parts by weight of disteardimonium hectorite, a spraying and mixing process performed at a pressure of 100 bar to 600 bar using a nozzle having a size of 1 μm to 50 μm, and a process of mixing components of an oil phase mixture at once using a 3-roll mil from Example 5.

Stability Comparison Experiment of Examples 5 and 6 and Comparative Example 3

After the sun sticks of Examples 5 and 6 and the sun stick of Comparative Example 2 were left at a temperature of 45° C. for 7 days, initial weights of the sun sticks were compared, and results thereof were shown in Table 3 below

TABLE 3

| Classification | Initial weight (g) | Weight after 7 days (g) |
| --- | --- | --- |
| Example 5 | 44.32 | 43.98 |
| Example 6 | 44.51 | 44.26 |
| Comparative Example 3 | 44.46 | 27.20 |

As shown in Table 3, in the case of Examples according to the present invention, there was almost no change in weight, but in the case of Comparative Example 3, most moisture was evaporated. Thus, it may be confirmed that formulation stability of the sun stick of the present invention is considerably excellent Example 7 (Vivistick)

0.5 parts by weight of polyglyceryl-4 isostearate, 0.5 parts by weight of polyglycerol-3 polyricinoleate, 0.5 parts by weight of sorbitan isostearate, 2.0 parts by weight of disteardimonium hectorite, and 1.5 parts by weight of cococaprylate/caprate (trade name Cetiol C 5C) were sprayed at a pressure of 100 bar to 600 bar using a nozzle having a size of 1 μm to 50 μm to be mixed into each other. As oil phase components, 7.5 parts by weight of ethylhexyl methoxycinnamate, 2 parts by weight of ethylhexyl salicylate, 2.5 parts by weight of octocrylene, 10 parts by weight of C12 to C15 alkyl benzoate (trade name: Saboderm AB), 5 parts by weight of butyloctyl salicylate, 5 parts by weight of bis-ethylhexyloxyphenol methoxyphenyl triazine, 8.5 parts by weight of ozokerite, 5.5 parts by weight of microcrystalline wax, 5 parts by weight of zinc oxide & triethoxycaprylylsilane (trade name SUNZnO-NAS), 6.56 parts by weight of titanium dioxide & alumina & triethoxycaprylylsilane (trade name SUNTITAN-AS), 1.08 parts by weight of yellow iron oxide & triethoxycaprylylsilane (trade name SUNIOY-AS), 0.23 parts by weight of red iron oxide & triethoxycaprylylsilane (trade name: SUNIOR-AS), and 0.13 parts by weight of black iron oxide & yriethoxycaprylylsilane (trade name: SUNIOB-AS) were mixed into the resultant mixture at a temperature of 70° C. to 75° C. using a 3-roll mill to prepare an oil phase mixture. 32.9 parts by weight of water, 1 part by weight of butylene glycol, 1 part by weight of glycerin, 1 part by weight of sodium chloride, and 0.1 parts by weight of disodium EDTAT were mixed at a temperature of 40° C. to prepare an aqueous phase component. The prepared oil phase mixture and aqueous phase component were stirred at a stirring speed ranging from 1,800 rpm to 2,500 rpm using a stirrer and mixed to manufacture a vivistick. The vivistick cosmetic was introduced into a mold and cooled to manufacture a final vivistick. Hardness was measured using SUN RHEO METER (manufactured by Sun Scientific Company (Japan)) and was in a range of 10 Newtons to 250 Newtons, which is suitable for stick cosmetics.

It will be understood by those skilled in the art that various changes in form and details may be made therein without departing from the spirit and scope of the invention as defined by the appended claims.

INDUSTRIAL AVAILABILITY

A water-releasing stick-type cosmetic according to the present invention may directly supply a large amount of moisture, have hardness suitable for stick cosmetics to have excellent formulation stability, have excellent spreadability, have excellent storage stability, and concurrently have excellent color tone.

The invention claimed is:

1. A water-releasing stick-type cosmetic comprising:
an oil phase portion; and
a moisture-releasing component spreading in the oil phase portion,
wherein the moisture-releasing component is characterized in that particles of moisture are surrounded by a plurality of plate-like materials to which an emulsifier is combined,
wherein the plate-like material is disteardimonium hectorite,
wherein the emulsifier includes a $C_9$ to $C_{22}$ alkyl residue,
wherein a content of the particles of moisture is in a range of 20 wt % to 60 wt %,
wherein a content of the plurality of plate-like material and a content of the emulsifier are included in a ratio of 0.9 to 10 parts by weight to 0.1 to 10 parts by weight,
wherein the particles of the moisture and the plurality of plate-like materials to which the emulsifier is combined are included in a ratio of 80 to 99 parts by weight to 1 to 20 parts by weight,
wherein a content of the oil phase portion is in a range of 0.001 wt % to 50 wt %,
wherein the plurality of plate-like materials, to which the emulsifier is combined, form a thixotropic polyhedron having a shape of 5-hedron to 500-hedron,
wherein the plate-like material has a height of 0.0005 μm to 0.005 μm,
wherein the particles of the moisture have a diameter of 1 μm to 100 μm, and
wherein the thixotropic polyhedron includes a plurality of pores, each pore having a maximum cross-sectional size which is within 50% of a maximum cross-sectional size of the particles of moisture.

2. The water-releasing stick-type cosmetic of claim 1, wherein the water-releasing stick-type cosmetic has a hardness of 10 Newtons to 250 Newtons.

3. The water-releasing stick-type cosmetic of claim 1, wherein the water-releasing stick-type cosmetic is used in a lipstick, a lip gloss, a lip balm, a lip tint, a vivistick, or a sun stick.

* * * * *